(12) United States Patent
Chen

(10) Patent No.: US 8,170,271 B2
(45) Date of Patent: May 1, 2012

(54) SYSTEM AND METHOD FOR TEST TUBE AND CAP IDENTIFICATION

(75) Inventor: Mo Chen, Liverpool, NY (US)

(73) Assignee: JADAK LLC, North Syracuse, NY (US)

( * ) Notice: Subject to any disclaimer, the term of this patent is extended or adjusted under 35 U.S.C. 154(b) by 980 days.

(21) Appl. No.: 12/145,619

(22) Filed: Jun. 25, 2008

(65) Prior Publication Data

US 2009/0324032 A1 Dec. 31, 2009

(51) Int. Cl.
*G06K 9/00* (2006.01)

(52) U.S. Cl. ........ 382/100; 382/128; 382/209; 382/190; 382/307

(58) Field of Classification Search ................... 382/100, 382/128, 190, 209, 370
See application file for complete search history.

(56) References Cited

U.S. PATENT DOCUMENTS

| | | | |
|---|---|---|---|
| 5,369,713 A | 11/1994 | Schwartz et al. | |
| 6,252,980 B1 | 6/2001 | Schwartz et al. | |
| 6,357,658 B1* | 3/2002 | Garczynski et al. | 235/462.01 |
| 6,518,542 B1 | 2/2003 | Robertson et al. | |
| 6,782,122 B1 | 8/2004 | Kline et al. | |
| 6,993,176 B2* | 1/2006 | Yamagishi et al. | 382/142 |
| 7,982,201 B2* | 7/2011 | Bryant et al. | 250/577 |
| 2005/0058350 A1* | 3/2005 | Dugan et al. | 382/224 |
| 2005/0169733 A1* | 8/2005 | Drynkin et al. | 414/404 |
| 2006/0178578 A1 | 8/2006 | Tribble et al. | |
| 2007/0286495 A1* | 12/2007 | Pine et al. | 382/209 |
| 2009/0067669 A1 | 3/2009 | Kojima | |
| 2009/0154764 A1 | 6/2009 | Khan et al. | |

FOREIGN PATENT DOCUMENTS

| | | |
|---|---|---|
| DE | 2733074 | 2/1979 |
| DE | 4109118 | 9/1992 |
| EP | 972744 A2 * | 1/2000 |
| EP | 1645838 | 4/2006 |
| GB | 2440818 | 2/2008 |
| WO | 2004065995 | 8/2004 |

* cited by examiner

*Primary Examiner* — Andrew W Johns
*Assistant Examiner* — Shefali Goradia
(74) *Attorney, Agent, or Firm* — David L. Nocilly; Bond Schoeneck & King

(57) ABSTRACT

A system for identifying test tube types and properties in a sample handling machine using visual information automatically obtained by an optical imager and then processed using vision processing methods. The system includes an optical imager positioned to capture images containing one or more test tubes in a rack and a microcontroller programmed to extract predetermined regions of interest and interpret the optical information in the image to decipher the dimension of the test tubes, determine the presence or absence of caps on the test tubes, decode any encoded data, and interpret custom symbologies. The system may then determine the nature of the test tubes or other containers presented before the image and provide that information to the sample handling machine to assist with processing of samples.

13 Claims, 12 Drawing Sheets

SYSTEM AND METHOD FOR TEST TUBE AND CAP IDENTIFICATION

BACKGROUND

1. Field of Invention

The present invention relates to machine vision systems and, more specifically, to a system and method for determining the nature of a test tube and associated cap using optical imaging techniques.

2. Background of the Art

Machine vision plays an important role in automated and robotic systems, such as assembly line manufacturing, quality control inspection, and sample processing. Conventional systems are generally comprised of an optical imager, such as a charged coupled device (CCD) or similar device using digital imaging technology, that is positioned to capture images of objects that pass in front of it. In low-light or enclosed applications, machine vision systems may include an illumination source, such as a bank of light emitting diodes (LEDs), positioned proximately to the imager. The images are subsequently processed to decode information contained in the resulting two-dimensional image, such as 1D linear codes, 2D stacked/matrix codes, OCR fonts, and postal codes. The image captured by the machine vision system may also be subjected to more advanced processing, such as shape recognition or detection algorithms, that provide information about the object of interest in the image. However, the characteristics of digital images taken by machine vision systems, such as the contrast of the image, often limit the processing techniques that may be employed and adversely affects the accuracy of the results obtained from the processing of the image contents.

In sample handling systems, such as blood analyzers and the like, samples are moved to and from diagnostic modules for automatic testing and retesting using a loading rack that holds a plurality of carriers, such as test tubes filled with samples. Proper identification of the samples, decoding of information encoded into labels on the test tube, recognition of the test tube type, and even determining whether the tube contains a cap may be critical for timely and accurate processing of samples.

SUMMARY OF THE INVENTION

It is a principal object and advantage of the present invention to provide a system and method for identifying the contents of image captured by a machine vision system.

It is an additional object and advantage of the present invention to provide a system and method for identifying the type of test tube in a rack handling system.

It is a further object and advantage of the present invention to provide a system and method for identifying whether a test tube in a rack handling system is associated with a cap.

Other objects and advantages of the present invention will in part be obvious, and in part appear hereinafter.

In accordance with the foregoing objects and advantages, the present invention comprises a system for identifying a test tube or other object that is presented to an optical imager as the test tube or object moves along an assembly line or process. In a preferred embodiment, the optical imaging platform is programmed to perform decoding of information contained within the image, such as any barcodes or recognizable symbology, as well as for more advanced image processing, such as pattern matching and shape detection, that allows for an accurate and efficient identification of the nature of the test tube or object, as well as any data or information encoded on barcodes or other indicia that are placed on the test tube. More particularly, the present invention comprises an optical imager for capturing images of at least one test tube positioned in a sample handling rack and a microcontroller associated with the optical imager for interpreting information contained in images captured by the imager. The microcontroller is preferably programmed to extract barcode information from captured images, extract information encoded into predetermined geometric symbologies in the images, and interpret visual information in regions of interest to determine whether a test tube is present and to identify the geometry of the test tube. In addition, the microcontroller is programmed to interpret visual information to determine whether a cap is present on the test tube, and then determine what type of test tube has been captured in the image. The information may then be provided to the main line processing of the sample handling machine to assist with identification and processing of samples.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
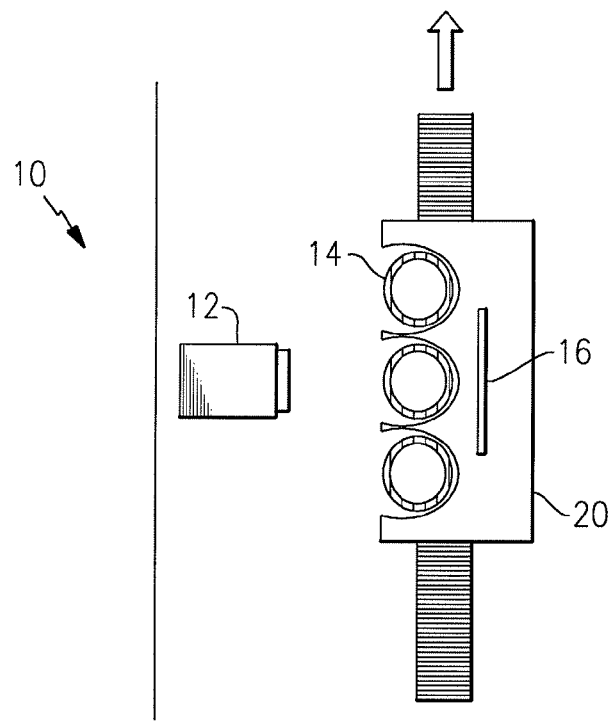
FIG. 1 is a schematic of a system for determining the nature of a test tube and associated cap in a sample handling device according to the present invention.

Referring now to the drawings, wherein like numerals refer to like parts throughout, there is seen in FIG. 1, a machine vision system 10 according to the present invention. System 10 comprises an optical imager 12 positioned on one side of a target, such as such as one or more test tubes 14. Preferably, a retro-reflective background 16 is positioned behind test tube 14 in alignment with imager 12 to reflect light onto the rear of tube 14.

Figure 2:
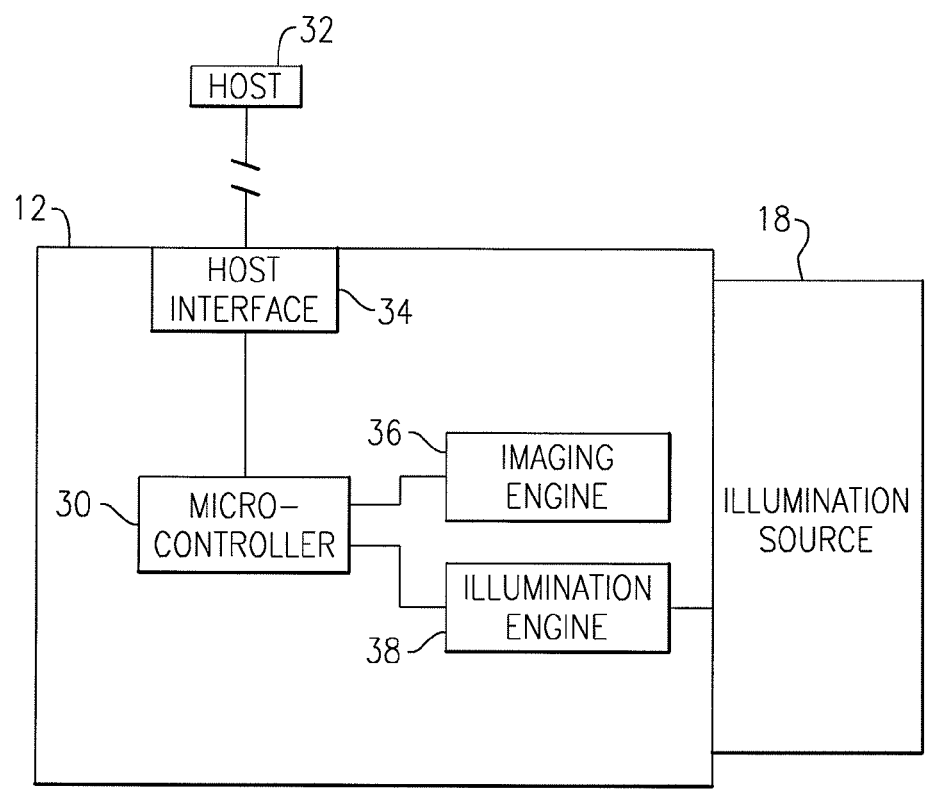
FIG. 2 is a schematic of an imager according to the present invention.

Imager 12 preferably comprises a complementary metal oxide semiconductor (CMOS) image sensor and is capable of reading and interpreting two-dimensional images, such as 1D linear codes, 2D stacked/matrix codes, OCR fonts, RSS (Reduced Space Symbology) codes, and postal codes, as well as provides image capturing for use in a wide range of applications, such as image and shape recognition, signature capture, image capture, and optical character recognition (OCR). As seen in FIG. 2, imager 12 may include an on-board illumination source 18 comprising one or more light emitting diodes (LEDs) of various wavelengths, to provide illumination of tube 14. For example, imager 12 may include red LEDs for general illumination and green LEDs for targeting. Illumination source 18 may be separately attached to imager 12 and positioned proximately thereto.

Imager 12 also includes a microcontroller 30 for managing imaging and illumination operations, performing processing of captured images, and communicating with a host 32, such as a host computer or a rack handling system, through a host interface 34. Host 32 preferably controls imaging of objects 14 based on host commands received from to host interface 34. Similarly, microcontroller 30 is capable of providing data to host device 32 via interface 34.

Host interface 34 may comprise a conventional RS232 transceiver and associated 12 pin FFC jack. Alternatively, interface 34 may comprise other conventional buses, such as USB, IEEE, 1394, IrDA, PCMCIA, or Ethernet (TCP/IP). Interface 34 may also comprise a wireless transceiver for wireless communication to a host computer and is programmed with the applicable protocols for interfacing with a host computer, such as Bluetooth® or 802.11 protocols. Microcontroller 30 is electrically connected to an imaging engine 36 for driving the optical imaging of a target object and receiving image data. Microcontroller 30 is also connected to an illumination engine 38 used for controlling timing and illumination source 18. Optionally, imaging engine 36 and illumination engine 38 may be provided in a single unit interconnected to microcontroller 30.

Imager 12 may comprise an IT4X10/80 SR/SF or IT5X10/80 series imager available from Hand Held Products, Inc. of Skaneateles Falls, N.Y. that is capable of scanning and decoding most standard barcodes including linear, stacked linear, matrix, OCR, and postal codes. The IT5X10/80 series imager is a CMOS-based decoded output engines that can read 2D codes, and has image capture capabilities. Imager 12 obtains an optical image of the field of view and, using preprogrammed algorithms, deciphers the context of the image to determine the presence of any decodable barcodes, linear codes, matrix codes, and the like. As will be explained hereinafter, imager 12 may further be programmed to perform other image processing algorithms, such as shape recognition, culling, match filtering, statistical analysis, and other high-level processing techniques, in addition to barcode detection. Microcontroller 30 may comprise a MC9328MXL VH15 microprocessor, available from Freescale Semiconductor, Inc. of Chandler, Ariz. that is programmed prior to implementation in imager 12, or programmed anytime thereafter, such as by using interface 34 to upgrade the firmware used to control microcontroller 30.

Reflective background 16 comprises a thin film or sheet having reflective properties that is aligned to reflect all or a portion of light emitting from illumination source 18 back to imager 12. Reflective background 16 preferably includes retroreflective characteristics. Positioning of reflective material 16 saturates the background, thus improving the contrast of the image taken by imager 12, allowing for the use of image processing techniques without the need for additional illumination sources or sophisticated illumination control circuitry. Preferably, reflective background 16 comprises seven millimeter retro-reflective sheeting. Sheeting generally comprises a layer of glossy mylar bonded to a liner by an adhesive, such as a layer of permanent acrylic. The layer of mylar and the layer of adhesive are preferably one millimeter thick each and the liner may comprise 90# polyethylene coated paper, resulting in a reflective sheeting of approximately seven millimeters in thickness. Acceptable reflective sheeting comprises the Series 680 Reflective Sheeting available from 3M of St. Paul, Minn.

Figure 3:
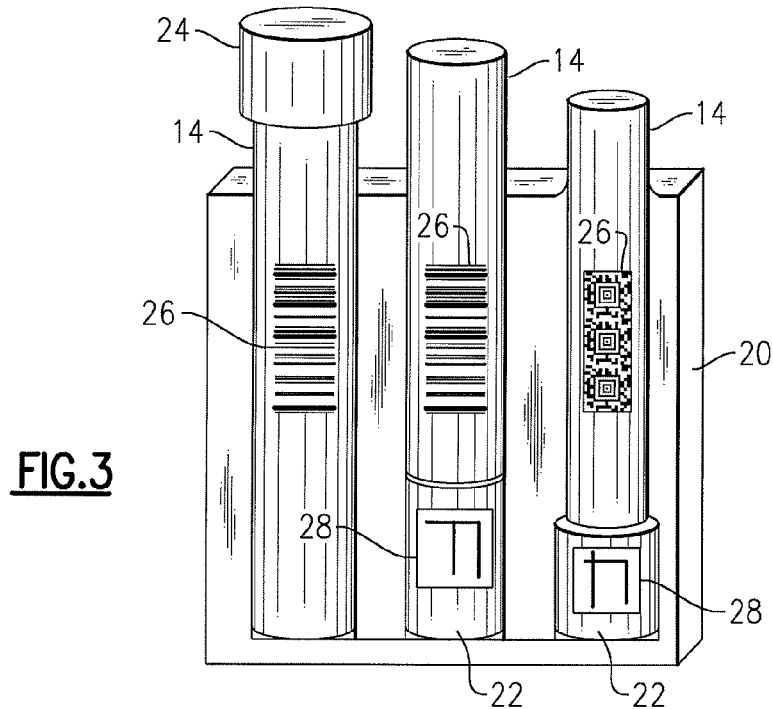
FIG. 3 is a schematic of a test tube and rack of a sample handling device according to the present invention.

Referring to FIG. 3, test tubes 14 may comprise any variety of shapes and sizes positioned in a rack 20. In some cases, tubes 14 may be positioned on top of an insert 22 positioned in rack 20, which are typically used to elevate tubes 14 for sample handling and processing. Test tubes 14 may include a cap 24 or similar device to contain fluids within tube 14. Tube 14 may further include a barcode 26 or comparable symbology placed on an intermediate portion of test tube 14. Insert 22 may include a label containing an indicia 28 to help with identification of tube 14, as will be explained in further detail herein. Indicia 28 preferably comprises a custom or predetermined symbology printed onto a retro-reflective label that is then adhered to insert 22 or even tube 14.

Figure 4:
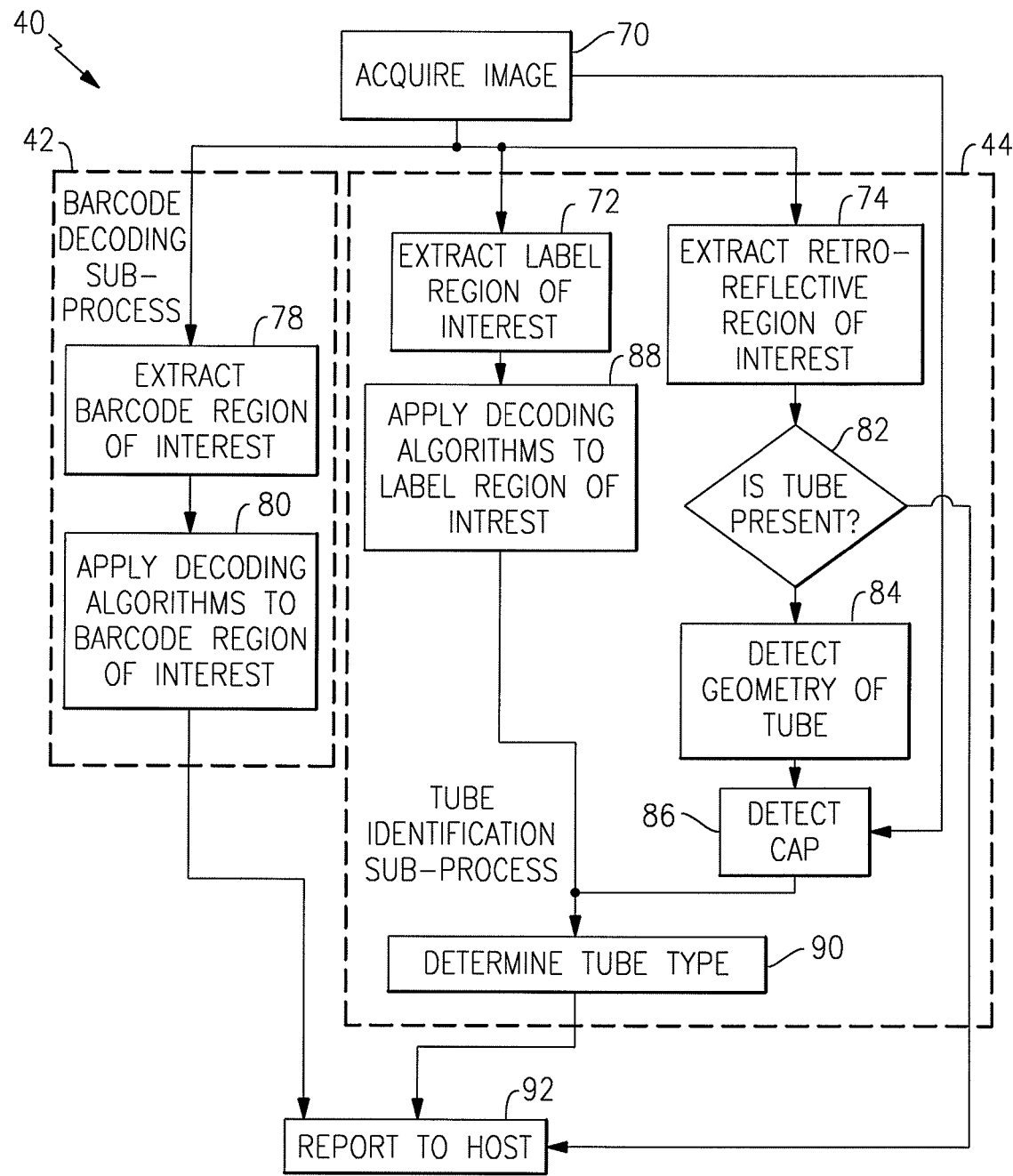
FIG. 4 is a high level flowchart of a machine vision process according to the present invention.

As seen in FIG. 4, microcontroller 30 may be programmed to execute an advanced machine vision process 40. Machine vision process 40 is preferably into two parallel sub-systems; a barcode decoding sub-process 42 and a tube identification sub-process 44. This separation of execution of barcode decoding sub-process 42 and tube identification sub-process 44 allows for flexibility. For example, barcode decoding sub-process 42 and tube identification sub-process 44 could be performed on two different processors to maximize processing speed.

Prior to performing machine vision process 40, microcontroller 30 must be configured using a calibration process 50 to ensure proper alignment of system 10 and to provide location information need for subsequent vision processing operations. Calibration process 50 is also implemented to provide the foundation for test tube identification according to the present invention and is necessary for identification of tube 14 and barcode 26 decoding, as well as for ensuring that rack 20 is properly aligned with respect to imager 12. For example, proper tube identification and barcode decoding rely on positioning of tube 14 near the center of a retro-reflective region created in a captured image as a result of the use of retro-reflective background 16, and ensuring that the retro-reflective region is rectangular, thereby verifying that the angle of imager 12 relative to tube 14 is correct. Calibration process 50 is thus responsible for analyzing a sample image and deducing the rectangle of the retro-reflective region and the offset of the center of the tube insert from the center the retro-reflective region.

Before commencing with calibration process 50, rack 20 must be positioned in front of imager 12 so that it can capture an image including the center of tube 14, as tube 14 preferably includes indicia 28 located in a central position so that calibration process 50 can easily identify the center of tube 14 by locating the center of indicia 28.

Figure 5:
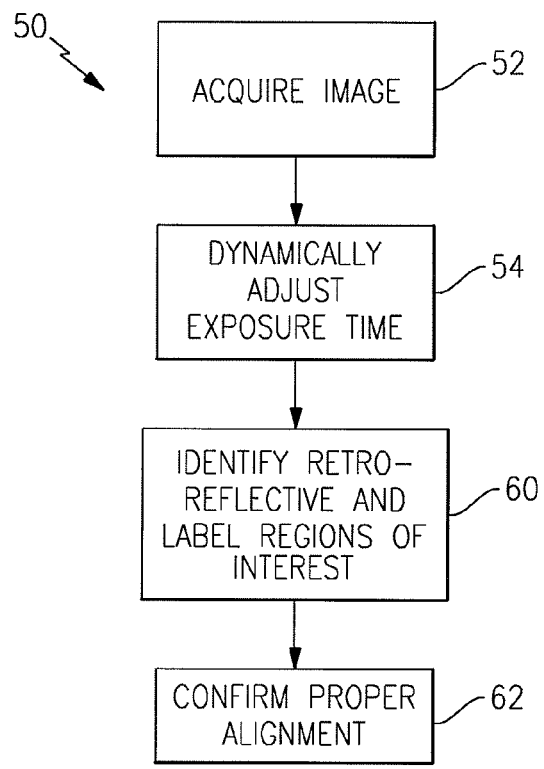
FIG. 5 is a flowchart of a calibration process according to the present invention
Figure 6:
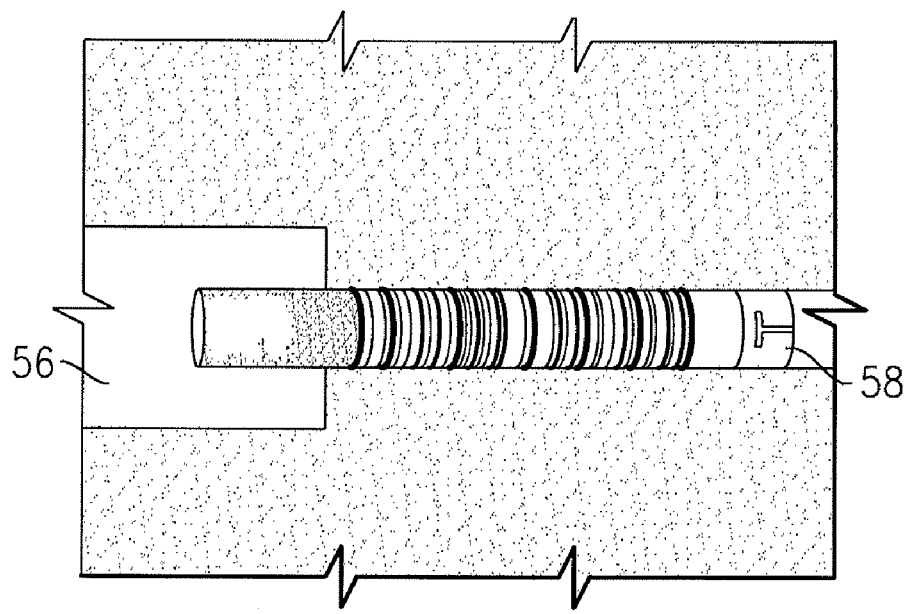
FIG. 6 is an image of a test tube according to the present invention.
Figure 7:
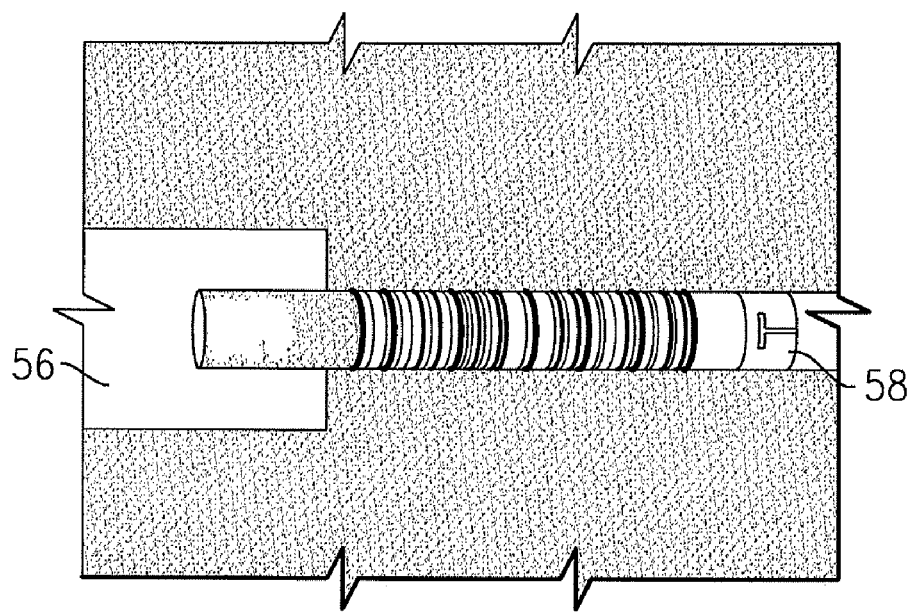
FIG. 7 is a processed image of a test tube according to the present invention.

Referring to FIG. 5, the first step in calibration process 50 is to acquire an image 52 that contains rack 20 and test tube 14 therein, including indicia 28 on tube 14, as illustrated in FIG. 6. The next step in process 50 is to dynamically adjust the exposure time 54 so that a retro-reflective region of interest 56 that surrounds the upper portion of tube 14 and a label region of interest 58 that contains indicia 28 are the largest and brightest regions within their respective portions of the captured image. As seen in FIG. 7, adaptive thresholding may used to segment the image into retro-reflective region of interest 56 and label region of interest 58.

Process 50 continues with the step of identifying the location 60 of retro-reflective region of interest 56 and label region of interest 58 with the image. By searching the thresholded image of FIG. 7, the bounding rectangles of retro-reflective region of interest 56 and label region of interest 58 can be deducted using either an image segmentation technique or a lateral histogram technique.

Figure 8:
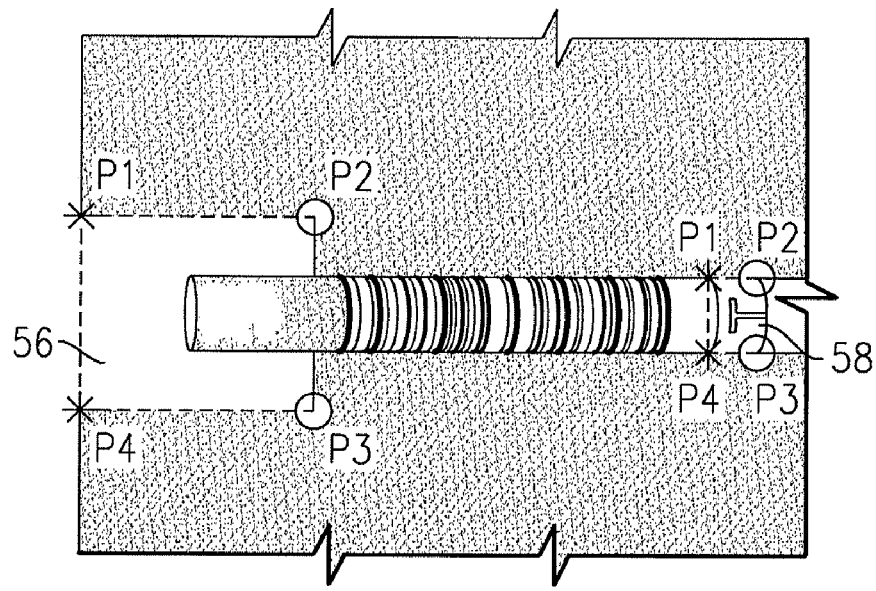
FIG. 8 is a further processed image of a test tube according to the present invention.

As unexpected specular reflection or misplaced test tubes 14 may inhibit these techniques from working properly, the predetermined rectangular shape and size of retro-reflective region of interest 56 and label region of interest 58 must be confirmed to determine the location of these regions. Confirmation begins by searching for four vertex points, identified as P1, P2, P3 and P4 in FIG. 8, that define rectangles that enclose retro-reflective region of interest 56 and label region of interest 58. The rectangle formed by the four vertex points is then checked by tracing and checking for any significant white lines connecting P1 and P2, connecting P1 and P4, and connecting P3 and P4. The significant white lines must be of sufficient length and devoid of any significant interruptions (or number of interruptions) to qualify. As seen in FIG. 8, the four points in the left side of the thresholded image define retro-reflective region of interest 56, while the average of the detected four points in the right side of the thresholded image provide the center of label region of interest 58.

The final step of calibration process 50 is to confirm proper alignment 62 using the location information provided by the processing explained above. The parameters of retro-reflective region of interest 56 (i.e., location, height and width), and the center of label region of interest 58 provide the requisite information to allow for proper horizontal and vertical alignment of imager 12. The offset dimension of retro-reflective region of interest 56 relative to label region of interest 58 will enable rack 20 to be moved to the correct horizontal position. In addition, the information may also be used to check if the parameters are in the tolerance range within which system 10 can perform normally. Once system 10 is properly calibrated using calibration process 50, the final locations of retro-reflective region of interest 56 and label region of interest 58 may be stored in memory in imager 12 for sequent vision processing functions so that retro-reflective region of interest 56 and label region of interest 58 may be extracted from a captured image and further processed. More specifically, the retro-reflective region of interest 56 is used for detecting the type of tube 14, and label region of interest 58 is used by system 10 for decoding indicia 28.

Figure 9:
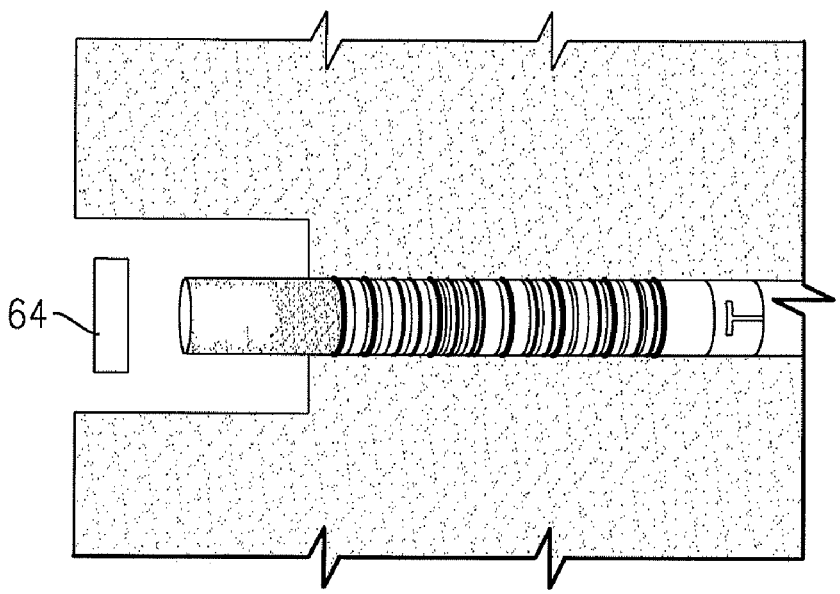
FIG. 9 is another processed image of a test tube according to the present invention.

Because of the retro reflective material, the backgrounds of both retro-reflective region of interest 56 and label region of interest 58 are quiet bright, i.e., near to saturation, which creates maximal contrast with the rest of the image. Due to such contrast, simple thresholding may be used to segment out the retro-reflective region of interest 56 and label region of interest 58. However, aging and drifting of the LEDs, damage to the reflective-material, and exterior lighting condition pose the potential threat to degrade this contrast. To correct for these variations, the exposure time of imager 12 may be adjusted by system 10 to ensure that the right background and contrast are used. Setting the exposure time is very important, because if it is set too high, the front tube object will be washed out. If the exposure is set too low, there will be a lot of noise appearing in retro-reflective region of interest 56. One solution is to adjust the exposure time dynamically to ensure that the right background and contrast are used. For example, whenever system 10 fails to identify tube 14 after calibration, system 10 may sample a test region 64 within retro-reflective region of interest 56 to see if it is uniform and bright enough, as seen in FIG. 9. If retro-reflective region of interest 56 is saturated, the exposure time may be decreased incrementally until tube 14 can be identified. Otherwise, the exposure time may be incremented until tube 14 is identified. The adjusted exposure time may then be saved and used in the tube identification process, as described below, until a failure is encountered. In the event of a failure, the operational exposure time may be dynamically adjusted until determining the proper exposure and saved for future use.

Once system 10 is calibrated and the operational exposure time is selected, as described above, machine vision process 40 may be executed. Referring to FIG. 4, the first step in process 40 is to acquire an image 70. Using the calibrated information, process 40 continues with the extraction 72 of retro-reflective region of interest 56 and extraction 74 of label region of interest 58. In addition, a barcode region of interest is extracted 78 from the image. Process 40 then continues with barcode decoding sub-process 42 and/or tube identification sub-process 44.

Barcode decoding sub-process 42 involves the application of conventional or commercially available barcode decoding algorithms 80 to barcode region of interest, such as those provided with the IT5X10/80 series imager identified above. Because any barcode 26 is positioned inside a predetermined region located in a predetermined relationship to retro-reflective region of interest 56 and label region of interest 58, system 10 may identify barcode region of interest using the calibration location information and provide such information to the onboard barcode decoder of imager 12 to expedite the barcode location process.

Tube identification sub-process 44 generally involves examining retro-reflective region of interest 56 to locate the top part of any tube 14 positioned therein to check whether a tube is present 82, determine the geometry 84 of the top of tube 14, and detect 86 any cap 20 positioned on tube 14. Tube identification sub-process 44 also searches for and applying the appropriate decoding algorithms 88 to decodes indicia 28 located in label region of interest 58. The extracted tube features, the binary decision of cap presence from retro-reflective region of interest 56, and decoded indicia 28 are then used as inputs to a rule-based decision system to determine the tube type 90. The determination of step 90, the determination that no tube is present at step 82, and/or the barcode information extracted at step 80 may then be reported 92 to host 32.

Figure 10:
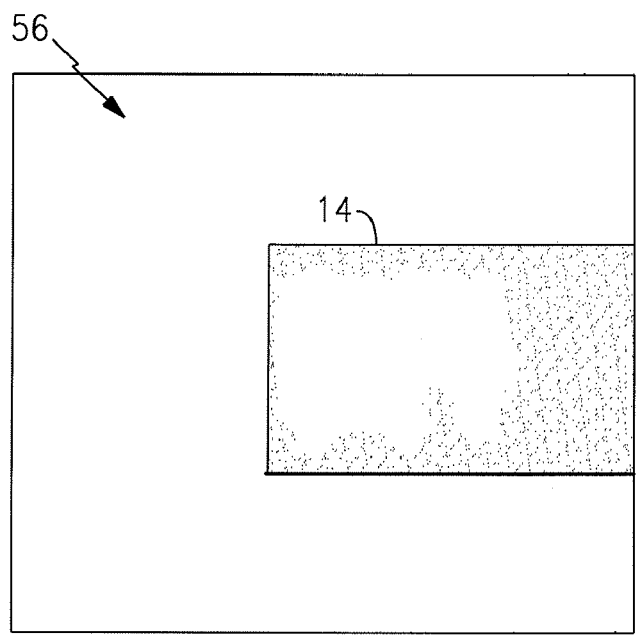
FIG. 10 is an image of a test tube region of interest according to the present invention.

With respect to step 84, once the system is calibrated and imaging exposure time is correctly set, the geometrical features of tube 14 can be easily recognized inside retro-reflective region of interest 56. An example of retro-reflective region of interest 56 is seen in FIG. 10. Edge detection is first performed on the retro reflective region of interest 56 to extract the boundary of the tube. An image pixel $f(x,y)$ is declared on the edge if it meets any of the following condition, $$abs(f(x,y)-f(x+1,y))>s_e$$

$$abs(f(x,y)-f(x+2,y))>s_e$$

$$abs(f(x,y)-f(x,y+1))>s_e$$

$$abs(f(x,y)-f(x,y+2))>s_e \quad (1)$$

where $f(x,y)$ stands for the image intensity at the $x^{th}$ row and the $y^{th}$ column, and abs(.) denotes the absolute function.

Figure 11:
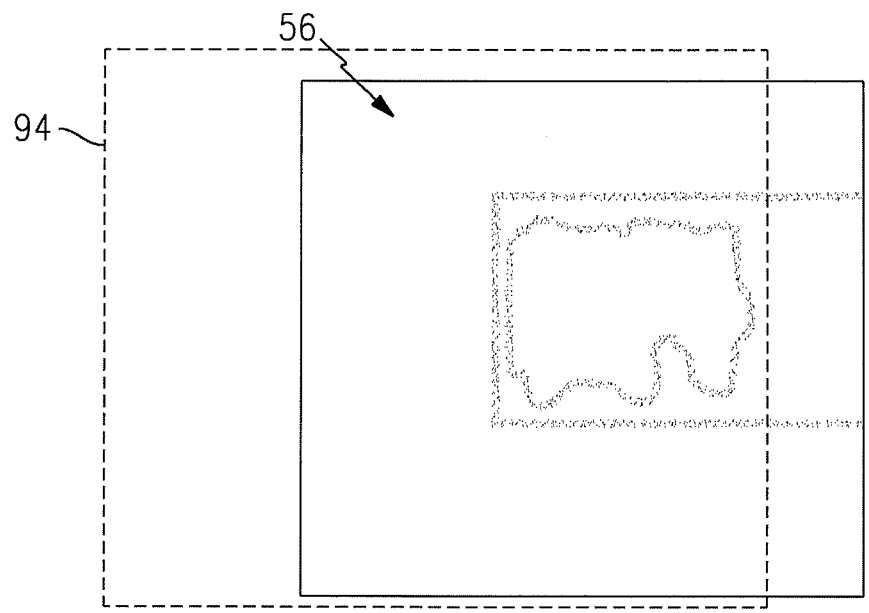
FIG. 11 is a processed image of a test tube region of interest according to the present invention.

The threshold $s_e$ defines what the level of image intensity transition can be regarded as edge. Instead of using the original sub-image of FIG. 10, $s_e$ is determined adaptively from the statistics of the processed image that is transformed from the original image using the robust image normalization. The robust image normalization is used to account for the potential illumination changes. The detected edge may be seen in FIG. 11, where the edge pixels and background pixels are represented by the black pixels and the white pixels, respectively. The edge detection is quiet simple and efficient since it does not require computing the high order statistics of the image. More sophisticated edge detection algorithms may be used for this purpose, but they generally do not improve accuracy significantly while consuming considerable time. Moreover, the above-described edge detection method can guarantee the detected edges are thick enough, which makes the later shape recognition more reliable. The edges may display some imperfect calibration and rack alignment, leading to some unwanted connected objects linking to the tube boundary that may confuse system 10. Therefore, system 10 preferably should isolate the connected tube boundary so that the geometrical features may be analyzed more correctly. Most of retro-reflective region of interest 56 is cropped (as shown by the dashed rectangle 94 in FIG. 11), so that on the inside the cropped version of the retro-reflective region 56 the objects on the top border and the bottom border will be disconnected from the tube boundary and can be removed using binary object segmentation techniques.

Figure 12:
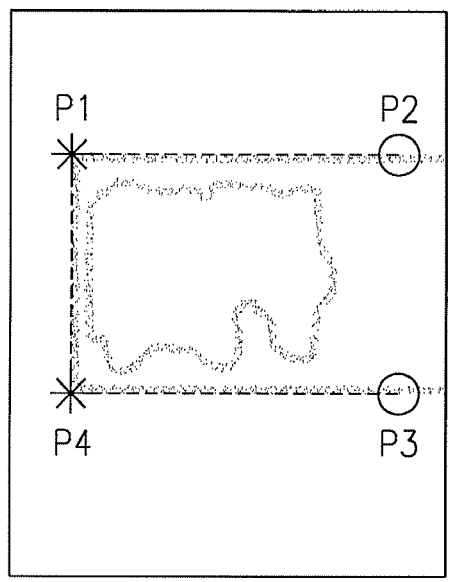
FIG. 12 is a further processed image of a test tube region of interest according to the present invention.

As with the calibration process, a simple algorithm may be used to extract the shape features of the tube. The operation of this algorithm is illustrated in FIG. 12, where system 10 detects the salient point P1, which is on the top-left corner of the tube edge. Starting from P1, system 10 then traces to the right until a few pixels from the right border of retro-reflective region of interest 56, and then checks if there is a connected edge (dashed line). The edge must be long enough and have interruptions less than a predefined number of pixels. In addition, the line connecting the start point P1 and the end point P2 must be parallel to the horizontal axis within a few degrees of tolerance. Using the same logic, the bottom salient point P4 may be detected on the left bottom corner of the tube edge, and a trace and check for a horizontal or near-horizontal edge (dashed line) to P3 (circle).

Figure 13:
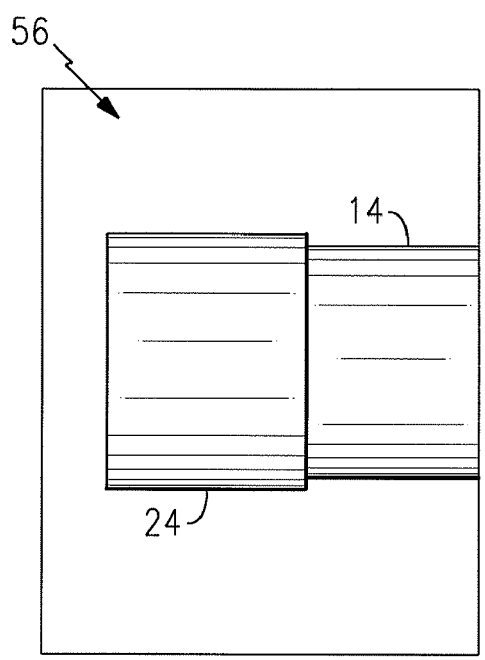
FIG. 13 is an image of a test tube cap region according to the present invention.
Figure 14:
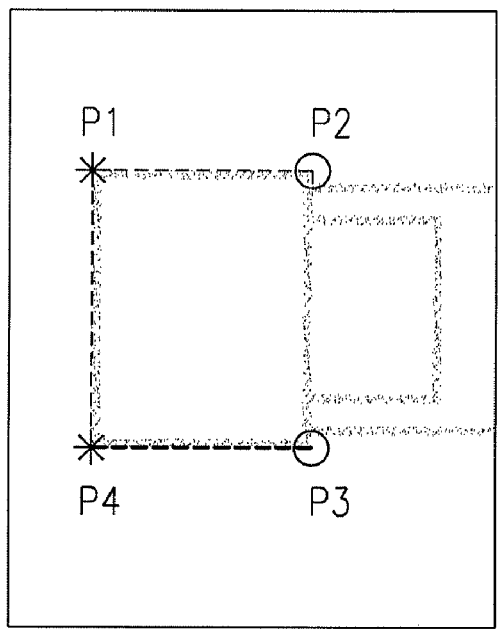
FIG. 14 is a processed image of a test tube cap region of interest according to the present invention.

There is seen in FIGS. 13-14, an example of the operation of this process on a test tube having a cap, where the points P2 and P3 are not linearly positioned with respect to the sides of tube 14 as in FIG. 12, but instead are positioned proximately to two concave bays at points P2 and P3 that are created by the presence of cap 24. This visual information may also be used by system 10 to determine the presence of the tube.

Locating the four salient points and evaluating their relative locations help system 10 determine the presence of tube 14 and the shape characters of tube 14. For example, the presence of all four salient points is the evidence that system 10 uses to determine if there is a tube 14 in rack 20. Second, if a tube 14 is found, the system 10 may perform a tube shape check on these four points (for example, if the column difference between the point P1 and P2 is found above the predefined threshold, system 10 can declare that either the tube is tilt or the cap is loose). Finally, system 10 uses these four points to deduct the tube geometry. For example, the height of the tube, in pixels, is determined as the average of the columns of P1 and P2. The height can be converted to inches or millimeters based on the projection matrix of imager 12, as trained in the calibration process.

Figure 15:
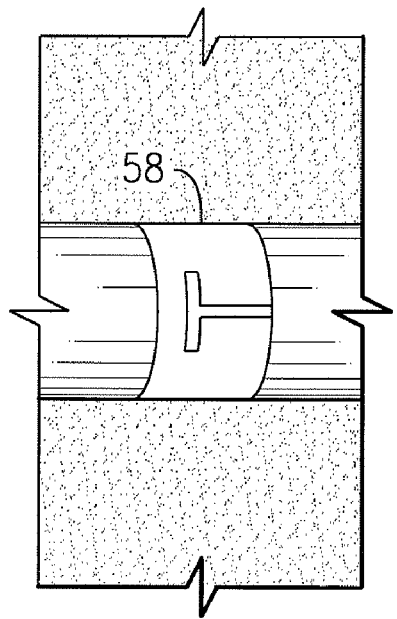
FIG. 15 is an image of an indicia region of interest according to the present invention.
Figure 16:
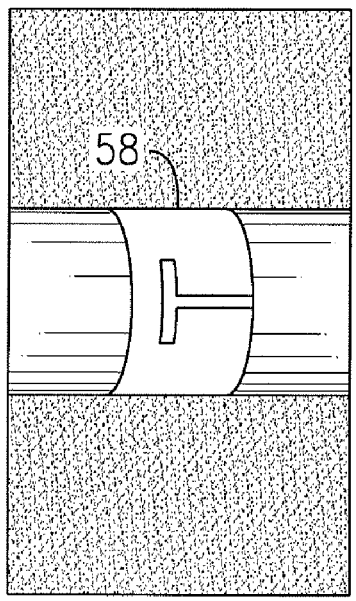
FIG. 16 is a processed image of an indicia region of interest according to the present invention.
Figure 17:
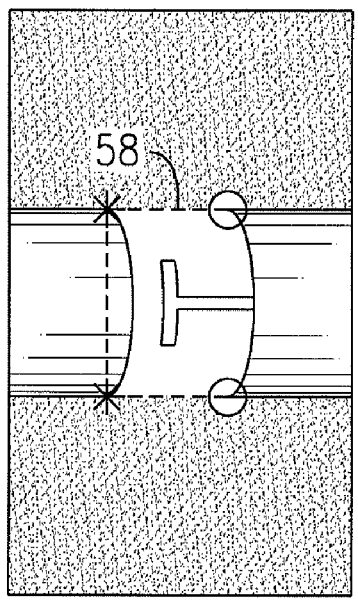
FIG. 17 is a further processed image of an indicia region of interest according to the present invention.
Figure 18:
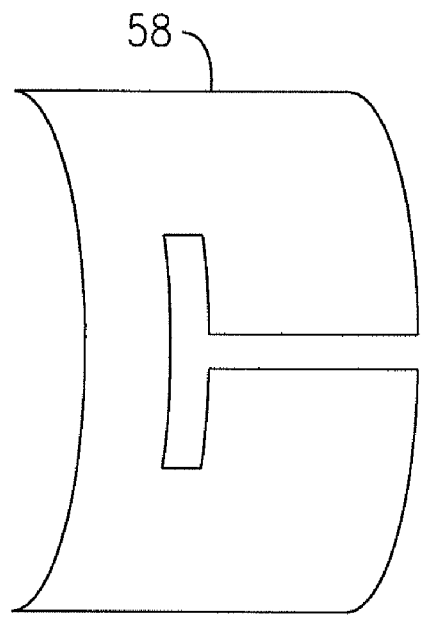
FIG. 18 is a yet further processed image of an indicia region of interest according to the present invention.

Tube identification sub-process 44 also searches for and decodes indicia 28 located in label region of interest 58. Indicia 28 is preferably a customized label that helps system 10 identify the type of the tube. For example, indicia 28 may comprise a label placed on an insert that is used to position tube 14 higher in rack 20, thereby bringing tube 14 into retro-reflective region of interest 56. As described above, calibration process 40 provides the center of label region of interest 58. Tube identification sub-process 44 can then extract 84 label region of interest 58, or at least a portion of the image captured at step 70 that is large enough to contain indicia 28, as seen in FIG. 15. Because indicia 28 preferably comprises retro-reflective material, indicia 28 will be a large, white object in comparison to a dark background. As with the calibration process, the step of decoding 84 first uses adaptive thresholding to segment out indicia 28, as seen in FIG. 16. Tube identification sub-process 44 may then apply a four-point method such as that described above to locate and extract label region of interest 58, as seen in FIG. 17. If no white object is found, or the found object is too small, tube identification sub-process 44 may determine that there are no indicia 28 and assign the corresponding flag to the tube identification decision-making process. If a likely indicia 28 is found, label region of interest 58 defined by the four points seen in FIG. 17 is extracted and the image morphology (binary erosion and dilation) is used to remove any small or noise-like objects to prune label region of interest 58. The de-noised label region of interest 58 is seen in FIG. 18.

Figure 19:
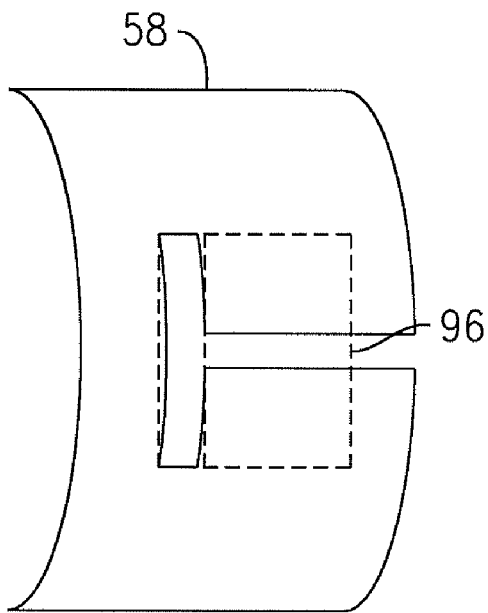
FIG. 19 is another processed image of an indicia region of interest according to the present invention.
Figure 20:
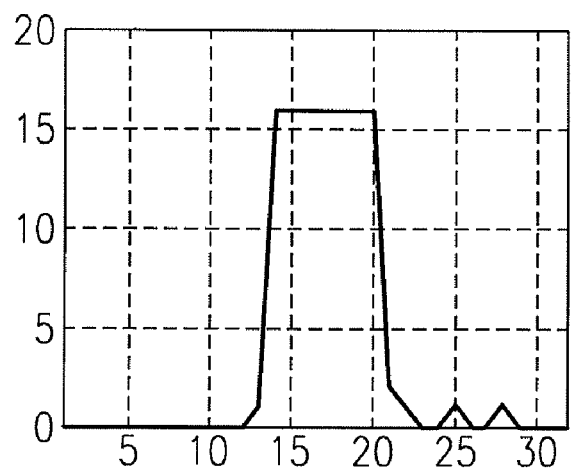
FIG. 20 is a vertical histogram of the image of FIG. 19.

Decoding of indicia 28 may then commence using a lateral histogram technique to locate any predetermined elements of indicia 28, as illustrated by rectangle 96 in FIG. 19 and resulting the vertical histogram seen in FIG. 20. For example, a custom symbology may include a number of icons comprised of various arrangements of geometric elements, such as horizontal and vertical bars. The identified geometric elements may then be verified against the specifications or standard used to define the symbols comprising acceptable indicia 28. It should be recognized by those of skill in the art that any conventional symbols may be used, or custom symbols developed specifically for the particular application of system 10.

Figure 21:
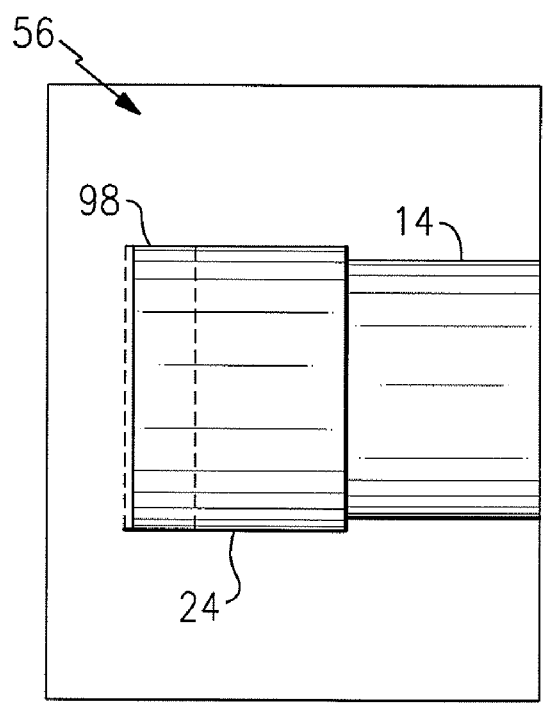
FIG. 21 is an image of a test tube region of interest according to the present invention.
Figure 22:
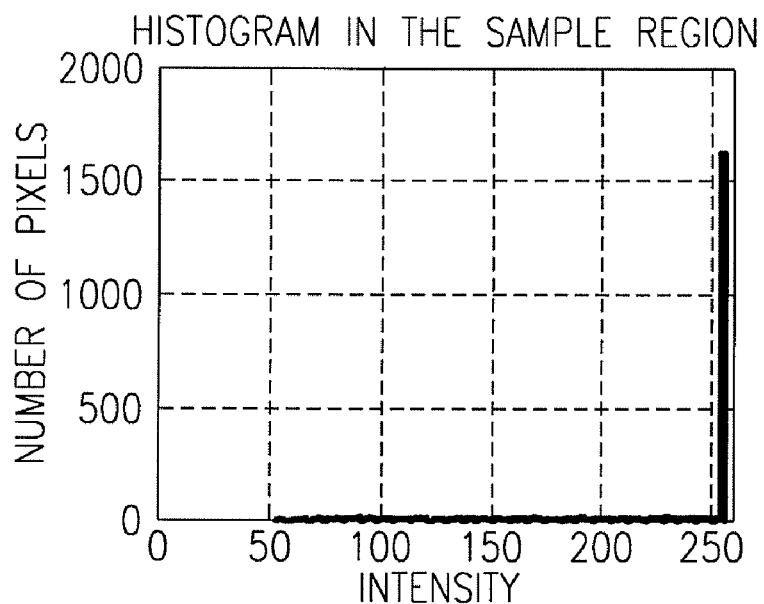
FIG. 22 is a histogram of a test tube region of interest in the absence of a cap.
Figure 23:
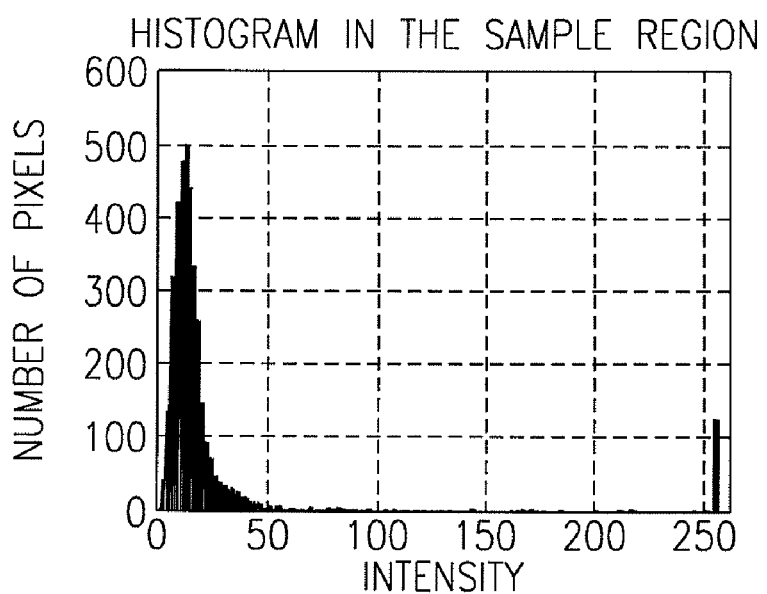
FIG. 23 is a histogram of a test tube region of interest in the presence of a cap.

Once tube 14 is detected and the tube height is determined, tube identification sub-process 44 may then perform cap detection 86 by analyzing the statistical characteristics of the image intensity in a cap sample region 98 at the very top region of tube 14, as seen in FIG. 21. As tubes 14 are generally transparent glass and caps are opaque plastic, transparent glass and opaque cap reflect light in different ways, thereby causing the image intensity inside cap sample region 98 for plain tubes 14 to be in one region of the histogram, as seen in FIG. 22, while the image intensity inside cap sample region 98 when a cap is present will takes up the other region of the histogram, as seen in FIG. 23. Therefore, by polling out the image intensity in cap sample region 98, system 10 may determine the presence or absence of a cap.

Aging and drifting of the LED lights and the translucent liquid residue that might adhere to the interior of the top of the tubes complicates the detection process by dragging the intensity of the cap sample region of the bare tube to the middle region of the histogram and may result in a failure to detect. One possible remedy for this problem is to increase the exposure time to such a level that the majority of the image intensity in the top region of the bare tube is saturated. On the contrary, no matter how high the exposure time is, the majority of the image intensity in the top region of the bare tube cannot be saturated. Accordingly, correct cap detection 86 may be performed by thresholding the saturation ratio (i.e., the number of saturated pixel to the total image pixels in the cap sample region). If the exposure time is increased enough to make the reliable cap detection, however, the front tube will be washed out and we cannot extract any shape information.

To address the conflicting requirements of the tube shape extraction and cap detection, system 10 is preferably configured to acquire a second, high exposure image of rack 20 at step 70. The first image acquired in step 70 using the operational exposure time is used to detect tube 14, decode any barcode 26, and decode indicia 28, while the second image of step 70 is used for cap detection 86. Based on the deducted shape information, e.g., the tube height, cap sample region 98 may be located and extracted from the high exposure image, and then processed to detect the presence or absence of cap 24.

Generally, items such as test tubes 14 are geometrically so simple that it is not possible to extract enough features from a captured image to distinguish different tube types. While a few primitive geometrical features, e.g., tube height, tube width, etc., may be extracted, these parameters do not provide enough information to distinguish the tube type because of the use of inserts below the test tubes and the presence or absence of tube caps. In order to properly classify the type of tube 14 in an application having multiple types, system 10 should preferably be able to discern the type of insert 22 used to raise tube 14 into position. Directly identifying the type insert 22 may be difficult because inserts 22 are often hidden in rack 20, and therefore hard to illuminate, and because barcodes 26 posted on tubes 14 and the liquid inside tubes 14 may obscure the transition between tube 14 and insert 22. Because the number of inserts 22 are generally limited, and the height of each insert 22 is known, a different indicia 28 may be assigned to each insert 22 and placed thereon so that system 10 can easily identify the insert type by decoding indicia 28. In the case of different style tubes 14 that are associated with the same insert, and thus the same indicia 28, the geometric information may be additionally considered to discriminate between the tube types.

It should be recognized that a simple rule-based decision algorithm may be implemented in microcontroller 30 to use the determined tube dimensions, cap presence or absence, and indicia to specifically identify one or more potential tube types in a particular system 10. For example, a database including a list of all possible tube types along with their respective parameters would allow for retrieval of a particular tube type based on the identification of one or more of the parameters that may be identified by system 10 as described above.

What is claimed is:

1. An apparatus for identifying a test tube, comprising:
   an imager for acquiring an optical image of the tube;
   a microcontroller associated with said imager;
   a host interface interconnected to said microcontroller; and
   wherein said microcontroller is programmed to identify the test tube in at least a portion of the optical image by
   extracting a first region of interest from the image;
   detecting a first set of features comprising the presence or absence of a cap in the first region of interest by cropping the first region of interest from the optical image, locating a set of points in the first region of interest, and comparing the location of the points against a predetermined standard;
   extracting a second region of interest from the optical image;
   detecting a second set of features of the test tube in the first region of interest;
   comparing the second set of detected features against a predetermined standard;
   and said microcontroller is further programmed to output information about the test tube through said host interface.

2. The apparatus of claim 1, wherein the first set of features further comprises the length and width of at least a portion of the test tube.

3. The apparatus of claim 2, wherein the second set of features comprise a custom indicia placed on the test tube.

4. The apparatus of claim 3, wherein said microcontroller is programmed to extract a third region of interest from the image and extract barcode information from the third region of interest.

5. The apparatus of claim 1, further comprising a reflective surface positioned to comprise a background to the test tube in said captured image.

6. The apparatus of claim 5, further comprising an illumination source associated with said imager and aligned to direct light onto the test tube when said optical image is acquired.

7. The apparatus of claim 6, wherein a portion of said directed light is reflected by the reflective surface back to said imager.

8. A method detecting the identity of a test tube, comprising:
   acquiring an optical image including the test tube;
   identifying a first region of interest in the image including the presence or absence of a cap on the test tube;
   detecting a first set of features in the first region of interest performing edge detection in the first region of interest to locate the test tube;
   cropping the image to remove areas outside of the first region of interest;
   extracting the first set of features from the image by locating a plurality of points in the image that define the outer geometry of the test tube;
   comparing the first set of features against a predetermined standard identifying the test tube based on the first set of features;
outputting the identity of the test tube.

9. The method of claim 8, wherein the first set of features further includes the width and length of at least a portion of the test tube.

10. The method of claim 8, further comprising the steps of:
identifying a second region of interest from the image;
detecting a second set of features in the second region of interest;
cropping the image to remove areas outside of the first and second region of interest;
extracting the second set of features from the image;
comparing the second set of features against a predetermined standard;
identifying the test tube based on the first and second set of features;
outputting the identity of the test tube.

11. The method of claim 10, further comprising the steps of
identifying a third region of interest from the image;
extracting barcode information from the third region of interest.

12. The method of claim 8, further comprising directing illumination toward one side of the test tube.

13. The method of claim 12, further comprising reflecting at least a portion of said illumination onto the opposite side of said test tube using a reflective background.

* * * * *